United States Patent [19]
Mallon et al.

[11] Patent Number: 5,319,113
[45] Date of Patent: Jun. 7, 1994

[54] PREPARATION OF LIQUID CRYSTALLINE DI(ALKOXYGLYCIDYL) COMPOUNDS, AND THEIR USE IN CURABLE EPOXIDE MIXTURES

[75] Inventors: Joseph J. Mallon, Stamford, Conn.; Paul M. Adams, Redondo Beach, Calif.

[73] Assignee: The Aerospace Corporation, El Segundo, Calif.

[21] Appl. No.: 74,094

[22] Filed: Jun. 9, 1993

Related U.S. Application Data

[62] Division of Ser. No. 937,615, Aug. 28, 1992, Pat. No. 5,237,076.

[51] Int. Cl.$^5$ ............... C07D 301/14; C07D 303/16; C07D 305/18
[52] U.S. Cl. .................................. 549/525; 549/561; 549/562
[58] Field of Search .......................... 549/525

[56] References Cited

U.S. PATENT DOCUMENTS

| | | | |
|---|---|---|---|
| 2,895,947 | 7/1959 | Shokal et al. | 549/562 |
| 2,907,726 | 10/1959 | Greenlee | 549/562 |
| 4,308,195 | 12/1981 | Mayer et al. | 549/561 |
| 4,386,191 | 5/1983 | DiSalvo et al. | 549/562 |
| 4,835,295 | 5/1989 | Walba et al. | 549/561 |
| 5,237,076 | 8/1993 | Mallon et al. | 549/525 |

FOREIGN PATENT DOCUMENTS

| | | | |
|---|---|---|---|
| 8112 | 2/1980 | European Pat. Off. | 549/525 |
| 44624 | 4/1979 | Japan | 549/525 |
| 789522 | 12/1980 | U.S.S.R. | 549/525 |

*Primary Examiner*—Joseph E. Evans
*Attorney, Agent, or Firm*—William J. Burke

[57] ABSTRACT

The invention relates to new, liquid crystalline di(alkoxyglycidyl) compounds of optionally ring substituted 1,4-dibenzoyloxybenzenes in which an alkoxy group consisting of 2 to 8 carbon atoms is incorporated between the glycidyl groups and the 1,4-dibenzoyloxybenzene, a synthesis of 4,4'-di(hexoxyglycidyl)-(1,4-dibenzoyloxybenzene), furthermore epoxy resin mixtures containing the new dialkoxyglycidyl compounds and the epoxy resin mixtures thereof in curable mixtures.

4 Claims, No Drawings

PREPARATION OF LIQUID CRYSTALLINE DI(ALKOXYGLYCIDYL) COMPOUNDS, AND THEIR USE IN CURABLE EPOXIDE MIXTURES

STATEMENT OF GOVERNMENT INTEREST

The invention was made with Government support under Contract No. F04701-88-C-0089 awarded by the Department of the Air Force. The Government has certain rights in the invention.

This application is a division of application Ser. No. 07/937,615, filed Aug. 28, 1982, now U.S. Pat. No. 5,237,076.

BACKGROUND OF THE INVENTION

1. Field of the Invention

The invention generally related to anisotropic curable monomors and in particular to anisotropic diglycidyl compounds.

2. Description of the Prior Art

Anisotropic heat-curable monomers are known which can be cured to form anisotropic thermoset resins. It is known to those skilled in the art that anisotropic thermoset resins, frequently processed from "liquid crystalline" polymers or monomers, have desirable self-reinforcing characteristics. U.S. Pat. Nos. 4,440,945, 4,452,993, and 4,514,553 (issued to Conciatori et al.) and U.S. Pat. No. 4,683,327 (issued to Stackman) disclose anisotropic heat-curable acetylene-terminated and acrylic-terminated monomers which can be formed into self-reinforcing thermoset resins as a result of molecular orientation in the cross-linked resin. However, the tendency of these monomers to self-condense precludes copolymerization with other monomers which are not acetylene-terminated or acrylic-terminated. U.S. Pat. No. 4,654,412 (issued to Calundann et al.) discloses base anisotropic polyesters containing stilbene or tolan functionalities which are copolymerized by the addition of comonomers ("curing agents") such as maleic anhydride to form anisotropic thermoset resins. The principal of copolymerization per se allows for the preparation of a vastly larger number of advantageous variations from the base anisotropic resin, but the temperatures and viscosities of the base resins are disadvantageously high.

U.S. Pat. No. 4,764,581 (issued to Müller et al.) relates to diglycidyl compounds of the formula (I)

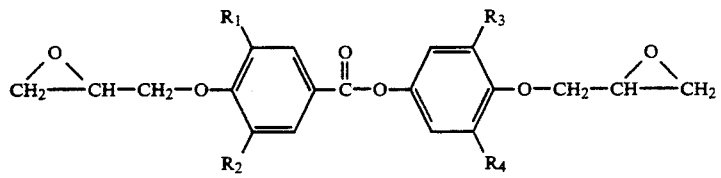

and discloses anisotropic liquid crystalline diglycidyl compounds which may be cured with a desirably wide variety of comonomers to form anisotropic thermoset resins. Furthermore, these compounds may be processed at desirably low viscosities and temperatures. This invention therefore retains the advantages of copolymerization cited above, but improves upon previous inventions by allowing more desirable processing conditions. However, the diglycidyl groups of this invention were linked directly to the 4-hydroxyphenyl 4-hydroxybenzoate group, such that the liquid crystalline character of the example cited ($R_1=R_2=R_3=R_4=H$) was only observed on cooling ("monotropic" liquid crystalline) and was only observed in a narrow 13° C. temperature range (from 93° C. to 80° C.). Hence, the "processing window" of these monomers which results in anisotropic thermoset resins is narrow and is only accessible on cooling. A broad window is not only desirable to facilitate advantageous processing, but also increases the number and type of curing agents which may be used, therefore advantageously expanding the versatility of the invention.

It is therefore desirable to provide anisotropic monomers which can be cured with a variety of curing agents to produce a range of useful products which exhibit self-reinforcing characteristics. It is furthermore desirable that the monomers be capable of forming an anisotropic phase when heated or cooled ("enantiotropic" liquid crystalline) that is maintained over a broad temperature range (wide processing window) so that mixtures of the monomers and various curing agents well known to those skilled in the art can be employed.

SUMMARY OF THE PRESENT INVENTION

The invention relates to new, liquid crystalline di(alkoxyglycidyl) compounds of optionally ring substituted 1,4-dibenzoyloxybenzenes in which an alkoxy group consisting of 2 to 8 carbon atoms is incorporated between the glycidyl groups and the 1,4-dibenzoyloxybenzene, a synthesis of 4,4'-di(hexoxyglycidyl)-1,4-dibenzoyloxybenzene, furthermore epoxy resin mixtures containing the new dialkoxyglycidyl compounds and the epoxy resin mixtures thereof in curable mixtures.

In accordance with the present invention, there are provided novel di(alkoxyglycidyl) monomers and curable mixtures thereof which display broad liquid crystalline melt phases on heating or cooling and a versatile method for the preparation of these.

DETAILED DESCRIPTION OF THE INVENTION

The deficiencies noted in the compounds disclosed in the previous invention of anisotropic diglycidyl compounds (U.S. Pat. No. 4,764,581) have been eliminated in the present invention by replacing the 4-hydroxyphenyl 4-hydroxybenzoate group with a 1,4-dibenzoyloxybenzene group and by incorporating an alkoxy group ("spacer") between the 1,4-dibenzoyloxybenzene group and the glycidyl groups. The above cited advantages of the previous invention have been retained. The present invention therefore relates to di(alkoxyglycidyl) compounds of the formula (II)

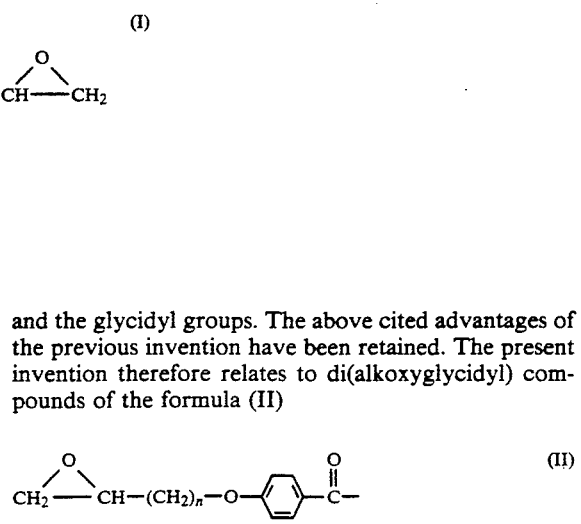

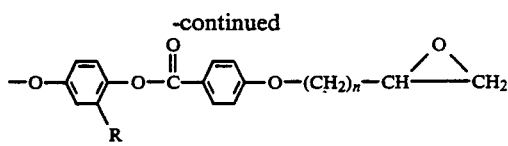

in which n is 2 to 8, preferably 3 to 6, and R denotes hydrogen, halogen, or alkyl having 1 to four carbon atoms, preferably 1 or 2 carbon atoms. Di(alkoxyglycidyl) compounds of optionally ring substituted 1,4-dibenzoyloxybenzenes were hitherto not known. It has been shown that these compounds have a broad, nematic, enantiotropic liquid crystalline character and thus make possible the construction of epoxy resins having particular physical properties.

The present invention also relates to a process for the preparation of di(alkoxyglycidyl) compounds of formula (II). The individual steps in the reaction are known in principle, and the current invention is characterized in that a ω-halo-1-alkene having from four to ten carbon atoms, preferably 5 to 8 carbon atoms, is reacted in a fashion known per se with an alkyl 4-hydroxybenzoate, said alkyl having from 1 to 4 carbon atoms. The resulting product is hydrolyzed with strong alkali in a fashion known per se to yield a 4-alkeneoxy benzoic acid. The 4-alkeneoxy benzoic acid is treated in a fashion known per se with alkylsulfonyl halide, thionyl halide, or other agents which remove the acidic hydrogen from the benzoic acid and replace it with a groups such as halogen or alkylsulfonyl halide which activate the carbonyl group for further reaction. The treated 4-alkeneoxy benzoic acid is reacted in a fashion known per se with a substituted dihydroxybenzene, such substituent being from the group hydrogen, halogen or alkyl having from 1 to 4 carbon atoms, preferably 1 to 2. The resulting 1,4-bis-(4-alkeneoxy) benzoate is treated in a fashion known per se with an oxidizing agent such as m-chloroperoxybenzoic acid or by other agents known by those skilled in the art to result in a glycidyl group.

The following method is preferably used: 1 mole of alkyl 4-hydroxybenzoate, 1 mole of ω-bromo-1-alkene, 0.05 mole of 18-crown-6 and 3 moles of potassium carbonate are reacted together in acetone at the boiling point. The solid product of this reaction is then hydrolyzed in boiling potassium hydroxide solution, isolated and 1 mole dissolved in 1,2-dimethoxyethane at 0° C., treated with 2 moles triethylamine, 1 mole methanesulfonyl chloride and 0.5 mole substituted dihydroxybenzene. One mole of the resulting 1,4-bis-(4-alkeneoxy) benzoate is then oxidized with 4 moles of m-chloroperoxybenzoic acid at 0° C., preferably in chloroform solvent, to yield di(alkoxyglycidyl) compounds of optionally ring substituted 1,4-dibenzoyloxybenzene. The oxidizing agent is normally m-chloroperoxybenzoic acid (MCPBA), but other oxidizing agents such as peracetic acid, perbenzoic acid, trifluoroperacetic acid, or 3,5-dinitroperoxybenzoic acid may alternatively be used for the conversion of the alkene groups to the glycidyl groups.

The present invention also relates to curable mixtures containing diglycidyl compounds of the formula (II), if appropriate as blends with di-, tri- and tetraglycidyl compounds which are known per se, and with curing agents for epoxy resins. The mixtures preferably contain at least 50% by weight and preferably at least 80% by weight of (II).

EXAMPLES

Example 1

The preparation of 4,4'-di(hexoxyglycidyl)-(1,4-dibenzoyloxybenzene) (formula II, n=6, R=H) is carried out in three steps as follows:

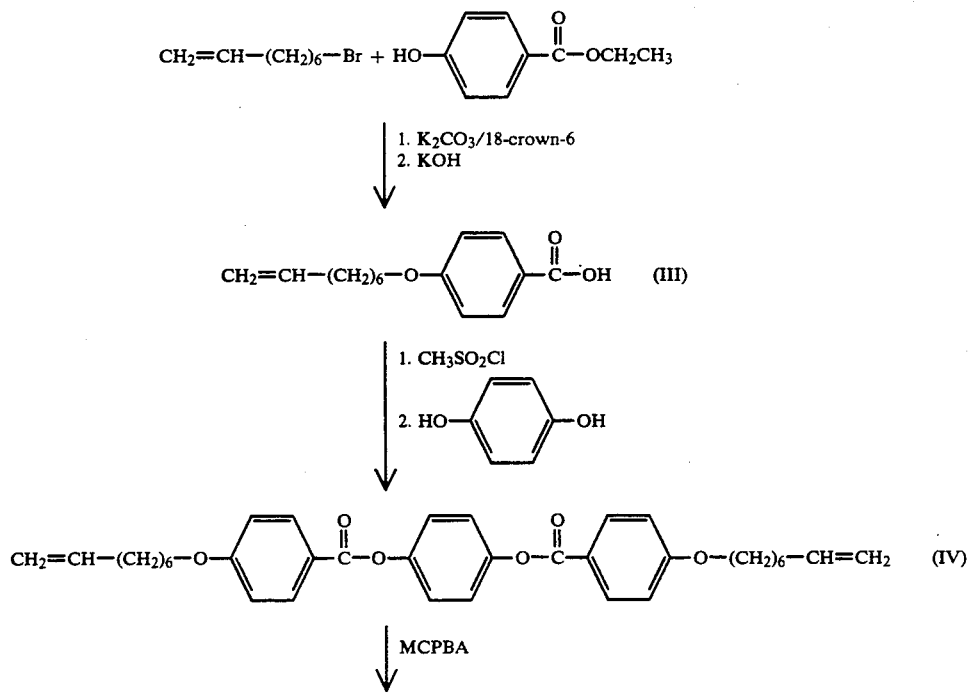

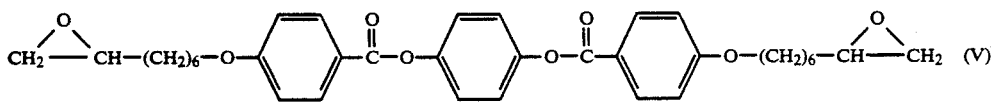

(III) 4-(7-octeneoxy) benzoic acid: 8-Bromo-1-octene (23.9 g, 0.125 mole), ethyl 4-hydroxybenzoate (18.28 g, 0.11 mole) and 18-crown-6 (1.35 g, 0.0055 mole) are dissolved in 150 ml of acetone in a 500 ml round-bottomed flask. Potassium carbonate (45.6 g, 0.33 mole) is added to the flask and the resulting mixture is stirred and refluxed for 24 hr. The mixture is filtered to remove the salts and the filtrate is evaporated under reduced pressure to yield a light yellow oil. 200 ml of 2M KOH is added to the oil and the resulting mixture is stirred and refluxed for five hours. The resulting clear yellow solution is cooled to room temperature and acidified with HCl. The resulting white precipitate is filtered off, washed with water, recrystallized from 125 ml of ethanol and dried under vacuum. Yield, 23.4 g (86% based on ethyl 4-hydroxybenzoate).

(IV) 1,4-Phenylene bis[4-(7-octeneoxy)benzoate]: (III) (23.59 g, 0.095 mole) is placed into 150 ml of 1,2 dimethoxyethane (dried over $CaH_2$) in a 500 ml round-bottomed flask. The resulting mixture is stirred and cooled to 0° C. under nitrogen. Triethylamine (19.23 g, 0.19 mole) and methanesulfonyl chloride (10.88 g, 0.095 mole) are added slowly, and the cooled mixture is stirred for 1.5 hr. A dimethoxyethane solution of hydroquinone (5.23 g, 0.0475 mole in 30 ml dimethoxyethane) is added dropwise to the cooled mixture over the course of 15 minutes. The resulting mixture is allowed to warm to room temperature and stirred for three hours. The mixture is filtered to remove a white solid and the filtrate and washings are combined and evaporated under reduced pressure to yield a waxy yellow solid. Recrystallization of the waxy solid from 125 ml of ethanol yielded, after vacuum drying, 14.12 g of white platelets. Yield, based on III, is 52%.

(V) 4,4'-Di(hexoxyglycidyl)-(1,4-dibenzoyloxybenzene): (IV) (14.27 g, 0.025 mole) is dissolved in 50 ml of $CHCl_3$ in a 250 ml round-bottomed flask. The resulting yellow solution is cooled to 0°-5° C. in an ice bath. m-Chloroperoxybenzoic acid (MCPBA, 17.26 g, 0.1 mole) is dissolved in 150 ml of $CHCl_3$ and added dropwise to the cooled solution. The resulting clear yellow solution is allowed to warm to room temperature and stirred for 4.5 hr, during which time a precipitate forms. The addition of 50 ml of $CHCl_3$ does not dissolve the precipitate. Petroleum ether (200 ml, bp 60°-90° C.) is added and the precipitate was filtered off. The filtrate is washed with dilute $NaHSO_3$, dilute $NaHCO_3$, dilute NaCl, and dried over $MgSO_4$. After confirming the absence of peroxide with a test strip, the solvent is removed under reduced pressure to yield a white solid. The solid is recrystallized twice from 125 ml of 90/10 ethanol/$CHCl_3$ to yield, after vacuum drying, 10.21 g of white crystalline powder. Yield, based on (IV), is 68%. The overall yield, based on ethyl 4-hydroxybenzoate, is 30%.

4,4'-Di(hexoxyglycidyl)-(1,4-dibenzoyloxybenzene) has a liquid crystalline character:

Differential scanning calorimetry (DSC) and polarized light microscopy (POM) measurements show that the crystalline compound changes into the nematic state at 107° C. and into the isotropic state at 190° C. The liquid crystalline phase is accessible on heating or cooling; i.e., the invention displays enantiotropic liquid crystalline behavior.

DSC was performed with a Mettler 3000 TC-10A instrument at a heating rate of 10° C. per minute and a cooling rate of 5° C. per minute with a nitrogen atmosphere. POM observations were carried out at 120X on a Zeiss microscope with a home-made hot stage.

EXAMPLE II (V)-PDA Curable mixtures of 4,4'-Di(hexoxyglycidyl)-(1,4-dibenzoyloxybenzene) and p-phenylenediamine: Dry mixtures of (V) and p-phenylenediamine (PDA) were prepared by dissolving 0.603 g ($1 \times 10^{-3}$ mole) of (V) and 0.054 g ($5 \times 10^{-4}$ mole) of PDA in 10 ml of $CHCl_3$, then immediately removing the solvent under reduced pressure at room temperature. The resulting solid was dried under vacuum and ground in a mortar and pestle to produce a fine white powder. Low temperature storage in a sealed container prevented the white powder from darkening.

(V)-PDA has a liquid crystalline character:

Differential scanning calorimetry (DSC) and polarized light microscopy (POM) measurements show that the crystalline compound changes into the nematic state at 101° C. and into the isotropic state at 180° C. The mixture is cured at 120° C. for four hours and postcured at 175° C. for three hours to produce a liquid crystalline anisotropic solid resin. The liquid crystalline character of the solid resin was confirmed by X-ray diffraction.

DSC was performed with a Mettler 3000 TC-10A instrument at a heating rate of 10° C. per minute and a cooling rate of 5° C. per minute with a nitrogen atmosphere. POM observations were carried out at 120X on a Zeiss microscope with a home-made hot stage. Wide angle X-ray diffraction (WAXD) patterns were obtained with nickel filtered copper $K_\alpha$ radiation using a commercially available (Blake Industries) evacuatable flat plate camera with pin-hole collimation. X-rays were produced by a Philips Electronics XRG3100 generator operated at 45 kV and 30 mA. With a nominal sample to film distance in the camera of 5 cm, exposure times of 1.5 hours were typical.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. Process for the preparation of compounds of the formula (II)

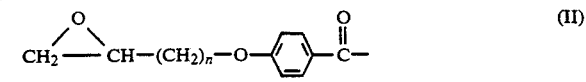

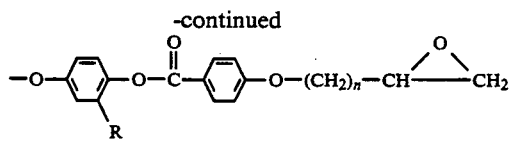

in which n is 2 to 8 and R denotes hydrogen, halogen or alkyl having 1 to 4 carbon atoms, said process comprising the steps of:
(a) reacting an ω-halo-1-alkene with an alkyl 4-hydroxybenzoate, where the ω-halo-1-alkene contains 4 to 10 carbon atoms;
(b) hydrolyzing the resulting product with alkali to yield a 4-alkeneoxy benzoic acid;
(c) activating the carbonyl group of the 4-alkeneoxybenzoic acid for further reaction by treating the 4-alkeneoxy benzoic acid with alkylsulfonyl halide or thionyl halide, thereby removing the acidic hydrogen from the benzoic acid and replacing it with halogen or alkylsulfonyl halide which activate the carbonyl group for further reaction;
(d) reacting the treated 4-alkeneoxybenzoic acid with a substituted 1,4-dihydroxybenzene where the substitute group is R;
(e) treating the resulting 1,4-phenylene-bis-(4-alkeneoxy) benzoate with an oxidizing agent to result in glycidyl groups.

2. The process claimed in claim 1 where the oxidizing agent is m-chloroperoxybenzoic acid.

3. The process as claimed in claim 1 where the alkylsulfonyl halide is methanesulfonyl chloride.

4. The process as claimed in claim 1 where R denotes hydrogen, halogen or alkyl having 1 or 2 carbon atoms.

* * * * *